United States Patent [19]

Casara et al.

[11] 4,260,823
[45] Apr. 7, 1981

[54] α-ACETYLENIC DERIVATIVES OF α-AMINO ACIDS

[75] Inventors: Patrick J. Casara, Strasbourg; Michel Jung, Illkirch Graffenstaden; Brian W. Metcalf, Strasbourg, all of France

[73] Assignee: Merrell Toruade et Compagnie, Strasbourg, France

[21] Appl. No.: 54,167

[22] Filed: Jul. 2, 1979

Related U.S. Application Data

[63] Continuation of Ser. No. 812,114, Jul. 1, 1977, abandoned.

[51] Int. Cl.³ .................. C07C 101/20; C07C 101/26; C07C 101/28; C07C 101/72
[52] U.S. Cl. .......................... 562/571; 260/112.5 R; 424/320; 424/309; 424/313; 424/314; 424/319; 424/246; 560/157; 560/159; 560/169; 560/171; 562/444; 562/448; 562/443; 562/561; 562/563; 544/19; 544/30; 542/419; 564/153
[58] Field of Search ..................... 560/71, 172, 39, 41, 560/157, 159, 171; 562/571, 565, 444, 443, 448, 561, 563; 260/112.5 R, 558 A, 561 A; 424/309, 319

[56] References Cited

U.S. PATENT DOCUMENTS

| 2,662,915 | 12/1953 | Lontz et al. ........................... 562/571 |
| 4,041,041 | 8/1977 | Metcalf et al. .................. 260/293.86 |

FOREIGN PATENT DOCUMENTS 559737 7/1958 Canada ..................... 562/571

OTHER PUBLICATIONS

Relyea et al., Biochem., Biophysics Res. Comm., 1975, 67(1), pp. 392–402.
Rando, Science, vol. 185, pp. 320–324 (1974).
Carlyle et al., Chem. Abst., vol. 80, #106132m, (1974).

Primary Examiner—James H. Reamer

Attorney, Agent, or Firm—John J. Kolano; Raymond A. McDonald; Salvatore R. Conte

[57] ABSTRACT

Novel acetylenic derivatives of α-amino acids of the following general structure:

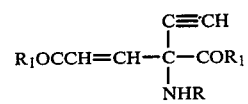

wherein R is hydrogen, alkylcarbonyl wherein the alkyl moiety has from 1 to 4 carbon atoms and is straight or branched, alkoxycarbonyl wherein the alkoxy moiety has from 1 to 4 carbon atoms and is straight or branched, or

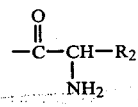

is hydrogen, a straight or branched lower alkyl group of 1 to 4 carbon atoms, benzyl or p-hydroxybenzyl; each $R_1$ is the same and is hydroxy, a straight or branched alkoxy group of from 1 to 8 carbon atoms, $-NR_3R_4$ wherein each of $R_3$ and $R_4$ is hydrogen or a lower alkyl group of from 1 to 4 carbon atoms and can be the same or different, or

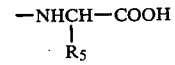

wherein $R_5$ is hydrogen, a straight or branched lower alkyl group of from 1 to 4 carbon atoms, benzyl or p-hydroxybenzyl; and pharmaceutically acceptable salts and individual optical isomers thereof.

6 Claims, No Drawings

α-ACETYLENIC DERIVATIVES OF α-AMINO ACIDS

This is a continuation of application Ser. No. 812,114, filed July 1, 1977, now abandoned.

FIELD OF INVENTION

This invention relates to novel α-acetylenic α-amino acid derivatives which are useful pharmacological agents and useful as intermediates.

SUMMARY OF INVENTION

Compounds of the following general Formula I are novel derivatives useful as antibacterial agents, as central nervous system excitatory agents and as intermediates for the preparation of useful cephalosporin derivatives:

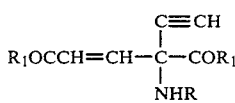

Formula I

In the above general Formula I each $R_1$ is the same and is hydroxy, a straight or branched alkoxy group of from 1 to 8 carbon atoms, $-NR_3R_4$ wherein each of $R_3$ and $R_4$ is hydrogen or a straight or branched lower alkyl group of from 1 to 4 carbon atoms and can be the same or different, or

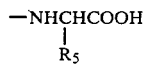

wherein $R_5$ is hydrogen, a straight or branched lower alkyl group of from 1 to 4 carbon atoms, benzyl or p-hydroxybenzyl; and R is hydrogen, alkylcarbonyl wherein the alkyl moiety has from 1 to 4 carbon atoms and is straight or branched, alkoxycarbonyl wherein the alkoxy moiety has from 1 to 4 carbon atoms and is straight or branched, or

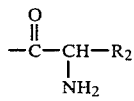

wherein $R_2$ is hydrogen, a straight or branched lower alkyl group of from 1 to 4 carbon atoms, benzyl or p-hydroxybenzyl.

Pharmaceutically acceptable salts of the compounds of general Formula I and individual optical isomers are included within the scope of the present invention.

DETAILED DESCRIPTION OF INVENTION

As used in general Formula I the term alkylcarbonyl is taken to mean the group

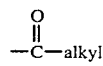

wherein the alkyl moiety has from 1 to 4 carbon atoms and is straight or branched, for example, methyl, ethyl, n-propyl, isopropyl, n-butyl, isobutyl and tert-butyl.

As used in general Formula I the term alkoxycarbonyl is taken to mean the group

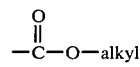

wherein the alkoxy moiety, that is, $-O$-alkyl, has from 1 to 4 carbon atoms and is straight or branched, for example, methoxy, ethoxy, n-propoxy, isopropoxy, n-butoxy, and tert-butoxy.

Illustrative examples of straight or branched alkyl groups having from 1 to 4 carbon atoms as used in general Formula I are methyl, ethyl, n-propyl, n-butyl, isopropyl and tert-butyl.

Illustrative examples of alkoxy groups having from 1 to 8 carbon atoms as used in general Formula I are methoxy, ethoxy, propoxy, butoxy, pentyloxy, and octyloxy.

Illustrative examples of pharmaceutically acceptable salts of the compounds of this invention include non-toxic acid addition salts formed with inorganic acids, such as, hydrochloric, hydrobromic, sulfuric and phosphoric acid, and organic acids, such as, methane sulfonic, salicylic, maleic, malonic, tartaric, citric and ascorbic acids; and non-toxic salts formed with inorganic or organic bases such as those of alkali metals, for example, sodium, potassium, and lithium, alkaline earth metals, for example, calcium and magnesium, light metals of Group III A, for example, aluminum, organic amines, such as, primary, secondary or tertiary amines, for example, cyclohexylamine, ethylamine, pyridine, methylaminoethanol, ethanolamine and piperazine. The salts are prepared by conventional means.

Preferred compounds of the present invention are those of general Formula I wherein each $R_1$ is hydroxy and within these preferred compounds the compound wherein R is hydrogen are more preferred.

Illustrative examples of compounds of the present invention are the following:

2-acetylene-3,4-dehydroglutamic acid,
2-acetylene-3,4-dehydroglutamic acid dimethyl ester,
2-acetylene-3,4-dehydroglutamic acid di-n-butyl ester,
2-acetylene-2-(1-oxopropyl)amino-3,4-dehydroglutaric acid,
2-acetylene-2-(1-oxoethyl)amino-3,4-dehydroglutaric acid diethyl ester,
2-acetylene-2-(2-amino-1-oxoethyl)amino-3,4-dehydroglutaric acid,
2-acetylene-2-methoxycarbonylamino-3,4-dehydroglutaric acid diamide, and
N,N'-di-n-propyl-2-acetylene-2-amino-3,4-dehydroglutaric acid diamide.

The compounds of this invention wherein $R_1$ of the α-carboxy group proximal to the acetylene function is hydroxy are useful as intermediates for the preparation of cephalosporin derivatives of the following general Formula II which are useful as antibacterial agents.

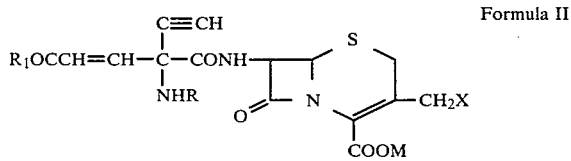

Formula II

In the above general Formula II, R and $R_1$ have the meanings defined in general Formula I; M is hydrogen or a negative charge and X is hydrogen or acetoxy.

The compounds of general Formula II and the pharmaceutically acceptable salts and individual optical isomers thereof are novel compounds useful as antibiotics and can be administered in a manner similar to that of many well known cephalosporin derivatives, for example, cephalexin, cephalothin, or cephaloglycine. The compounds of general Formula II and pharmaceutically acceptable salts and isomers thereof can be administered alone or in the form of pharmaceutical preparations either orally or parenterally and topically to warm blooded animals, that is, birds and mammals, for example, cats, dogs, bovine cows, sheep, horses and humans. For oral administration the compounds can be administered in the form of tablets, capsules or pills or in the form of elixirs or suspensions. For parenteral administration, the compounds may best be used in the form of a sterile aqueous solution which may contain other solutes, for example, enough saline or glucose to make the solution isotonic. For topical administration the compounds of general Formula II, salts and isomers thereof may be incorporated into creams or ointments.

Illustrative examples of bacteria against which the compounds of general Formula II and the pharmaceutically acceptable salts and individual optical isomers thereof are active are *Staphylococcus aureus, Salmonella schotmuehleri, Klebsiella pneumoniae, Diplococcus pneumoniae* and *Streptococcus pyogenes.*

Illustrative pharmaceutically acceptable non-toxic inorganic acid addition salts of the compounds of general Formula II are mineral acid addition salts, for example, hydrogen chloride, hydrogen bromide, sulfates, sulfamates, phosphate, and organic acid addition salts are, for example, maleate, acetate, citrate, oxalate, succinate, benzoate, tartrate, fumarate, malate and ascorbate. The salts can be formed by conventional means.

Illustrative examples of compounds of general Formula II are 7-[[2-acetylene-2-amino-4-carboxy-3,4-dehydrobutyryl)amino]-3-acetyloxymethyl-8-oxo-5-thia-1-azabicyclo[4.2.0]oct-2-ene-2-carboxylic acid and 7-[[2-acetylene-2-amino-4-methoxycarbonyl-3,4-dehydrobutyryl]amino]-3-acetyloxymethyl-8-oxo-5-thia-1-azabicyclo[4.2.0]oct-2-ene-2-carboxylic acid.

The preparation of the compounds of general Formula II is described hereinbelow.

The compounds of general Formula I are useful as central nervous system excitatory agents, or central nervous system stimulants, and anti-bacterial agents, or microbicides. The compounds of general Formula I are also irreversible inhibitors of glutamic acid decarboxylase the enzyme which catalyzes in vivo the conversion of glutamic acid to γ-aminobutyric acid. As microbicides the compounds of general Formula I are useful in the control of microorganisms such as *E. coli* and other microorganisms which contain glutamic acid decarboxylase.

The utility of compounds of general Formula I as irreversible inhibitors of glutamic acid decarboxylase in vivo may be demonstrated as follows. A compound of general Formula I is administered to rats or mice as an aqueous solution or suspension orally or parenterally. At varying time intervals after administration of the test compound the animals are decapitated and their brains homogenized in phosphate buffer. Glutamic acid decarboxylase activity in these homogenates is measured as described by M. J. Jung et al., J. Neurochem. 28, 717–723 (1977).

As irreversible inhibitors of glutamic acid decarboxylase the compounds of general Formula I provide a means of studying the physiological role of γ-aminobutyric acid.

As pharmacologically useful agents the compounds can be administered in various manners to the patient being treated to achieve the desired effect. The compounds can be administered alone or in the form of a pharmaceutical preparation orally, parenterally, for example, intravenously, intraperitoneally, or subcutaneously, or topically. The amount of compound administered will vary over a wide range and can be any effective amount. Depending on the patient to be treated, the condition being treated and the mode of administration, the effective amount of compound administered will vary from about 0.1 mg/kg to 250 mg/kg of body weight of the patient per unit dose and preferably will be about 1 mg/kg to about 50 mg/kg of body weight of patient per unit dose. For example, a typical unit dosage form may be a tablet containing from 10 to 300 mg of a compound of Formula I which may be administered to the patient being treated 1 to 4 times daily to achieve the desired effect.

As used herein the term patient is taken to mean warm blooded animals such as mammals, for example, cats, dogs, rats, mice, guinea pigs, sheep, horses, bovine cows, and humans.

The solid unit dosage forms can be of the conventional type. Thus, the solid form can be a capsule which can be of the ordinary gelatin type containing a novel compound of this invention and a carrier, for example, lubricant and inert fillers such as lactose, sucrose and corn starch. In another embodiment, the novel compounds are tableted with conventional tablet bases such as lactose, sucrose or corn starch in combination with binders such as acacia, corn starch or gelatin, disintegrating agents such as corn starch, potato starch, or alginic acid, and a lubricant such as stearic acid, or magnesium stearate.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable or synthetic origin, for example, peanut oil, soybean oil, and mineral oil. In general, water, saline, aqueous dextrose, and related sugar solutions, ethanols and glycols such as propylene or polyethylene glycol are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber manufactured by the Dow-Corning Corporation.

The compounds of general Formula I wherein each $R_1$ is hydroxy are prepared by treating lower alkyl 2-tri-(lower)alkylsilylacetylene-N-carbethoxyglycinate with a strong base and alkylating the thus formed dianion with methyl-trans-3-chloroacrylate in the suitable solvent in the presence of a complexing agent such as N,N,N',N'-tetramethylethylenediamine or hexamethylphosphortriamide followed by acid hydrolysis. The lower alkyl groups are straight or branched and have from 1 to 4 carbon atoms, for example, methyl, ethyl, n-propyl or tert-butyl.

The alkylating reaction may be carried out in aprotic solvent, for example, benzene, toluene, ethers, tetrahydrofuran, dimethylsulfoxide, or mexamethylphosphoramide. The reaction temperature varies from about −120° to about 25° C., a preferred reaction temperature being about −70° C. The reaction time varies from about ½ hour to about 24 hours.

The hydrolysis step can be achieved by treatment with aqueous acid, for example, hydrochloric acid. The alkylating reagents are commercially available or can be prepared by procedures known in the art.

Suitable strong bases for the above reaction are, for example, alkyl lithium, such as, butyl lithium or phenyl lithium, lithium dialkylamide, such as, lithium diisopropylamide, lithium amide, tertiary potassium butylate or sodium amide.

The reactant lower alkyl 2-tri(lower)alkylsilylacetylene-N-carbethoxyglycinates are prepared by reacting one equivalent of lower alkyl N-carbethoxy-2-chloroglycinate with one equivalent of 2-tri-(lower)alkylsilylacetylene in the presence of aluminum chloride. Lower alkyl N-carbethoxy-2-chloroglycinates are prepared by the general procedure described by U. Zoller and B. Ben-Ishai, Tetrahedron, 31, 863 (1975) only substituting ethyl carbamate for benzyl carbamate.

The compounds of this invention wherein $R_1$ is a straight or branched alkoxy group of from 1 to 8 carbon atoms are prepared from the corresponding derivatives wherein $R_1$ is hydroxy by reaction with an alcohol of the formula $R_6OH$ wherein $R_6$ is a straight or branched alkyl group of from 1 to 8 carbon atoms, saturated with HCl gas at about 25° C. for from about 12 to 36 hours.

The compounds of general Formula I wherein each $R_1$ is a straight or branched alkoxy group of from 1 to 8 carbon atoms may also be prepared by converting the corresponding compound wherein $R_1$ is hydrogen to the acid halide by, for example, treatment with thionyl chloride, followed by alcoholysis with an alcohol of the formula $R_6OH$ as defined above by procedures generally known in the art.

The compounds of Formula I wherein each $R_1$ is $NR_3R_4$ and each of $R_3$ and $R_4$ is hydrogen or a straight or branched lower alkyl group of 1 to 4 carbon atoms are prepared by an acylation reaction of an acid halide, for example, an acid chloride, of the corresponding compound wherein each $R_1$ is hydroxy and R has the meaning defined in Formula I with the proviso that any free amino group is suitably protected with protecting groups, such as, carbobenzyloxy or tert-butoxycarbonyl, with an appropriate amine which may be represented as $HNR_3R_4$. The reaction is carried out in methylene chloride, chloroform, dimethylformamide, ethers, such as, tetrahydrofuran or dioxane, or benzene at about 25° C. for about 1 to 4 hours. Suitable amines are ammonia, or a compound which is a potential source of ammonia, for example, hexamethylenetetramine; primary amines, for example methylamine, ethylamine, or n-propylamine; and secondary amines, for example, dimethylamine, diethylamine or di-n-butylamine. Following the acylation reaction the protecting groups are removed by treatment with acid, for example, trifluoroacetic acid or hydrogen bromide in dioxane.

The compounds of general Formula I wherein each $R_1$ is

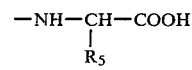

are prepared by reacting the corresponding derivative wherein each $R_1$ is hydroxy or a functional derivative thereof such as an acid anhydride and R has the meaning defined in Formula I with the proviso that any free amino group in protected with a suitable blocking group, such as, benzyloxycarbonyl, tert-butoxycarbonyl with a compound of the formula

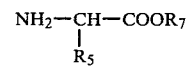

wherein $R_5$ has the meaning defined in general Formula I and $R_7$ is a lower alkyl group, for example, methyl or ethyl in an ether solution, such as, tetrahydrofuran or dioxane at 0° to 50° C. for 1 to 24 hours followed by acid hydrolysis with, for example, trifluoroacetic acid or hydrogen bromide in dioxane for about 1 to 20 hours to remove the protecting group, with the proviso that when the amine protected free acid is employed the reaction is carried out using a dehydrating agent such as dicyclohexylcarbodiimide.

The compounds of general Formula I wherein R is alkylcarbonyl wherein the alkyl moiety is straight or branched and has from 1 to 4 carbon atoms are prepared by treating the corresponding derivative wherein R is hydrogen and $R_1$ is hydroxy with an acid halide of the formula

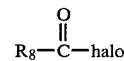

wherein halo is a hlaogen atom, for example, chlorine or bromine and $R_8$ is a straight or branched alkyl group having from 1 to 4 carbon atoms or an appropriate acid anhydride in water in the presence of a base such as sodium hydroxide or sodium borate at a temperature of from 0° to about 25° C. for from ½ hour to about 6 hours. These compounds may also be prepared from the ester derivative, that is, compounds of general Formula I wherein R is hydrogen and each $R_1$ is an alkoxy group of from 1 to 8 carbon atoms by treatment with the acid halide,

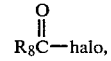

described above, or an appropriate acid anhydride in water, methylene chloride, chloroform or dimethyl acetamide in the presence of a base such as sodium hydroxide, potassium hydroxide or excess triethylamine at a temperature of from 0° to about 25° C. for from ½ hour to about 24 hours.

The compounds of general Formula I wherein R is alkoxycarbonyl wherein the alkoxy moiety is straight or branched and has from 1 to 4 carbon atoms are prepared by treating the corresponding derivative wherein R is hydrogen and each $R_1$ is hydroxy with a halo alkylformate of the formula

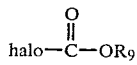

wherein halo is a halogen atom such as chlorine or bromine and $R_9$ is a straight or branched alkyl group having from 1 to 4 carbon atoms in water in the presence of a base such as sodium hydroxide or sodium borate at a temperature of from 0° to about 25° C. for from ½ hour to about 6 hours.

The compounds of general Formula I wherein R is

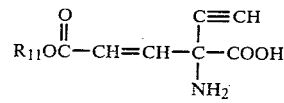

Formula IV or a functional derivative thereof, such as, the acid chloride or an acid anhydride in the presence of a dehydrating agent such as dicyclohexyl carbodiimide wherein $R_{11}$ is benzyl, and the amino group is protected by suitable blocking groups, for example, tert-butoxycarbonyl followed by acid hydrolysis to remove the amino protecting groups and the tert-butyl or benzyl group resulting in a carboxy derivative.

(0.005 mole) of methyl 2-trimethylsilylacetylene-N-carbethoxyglycinate. After 30 minutes at −70° C. 600 mg (0.005 mole) of methyl-trans-3-chloroacrylate (H. O. House, et al, J. Org. Chem. 31, 646 (1966)) is added and the solution is maintained at −70° C. for 30 minutes. The mixture is then neutralized using aqueous ammonium chloride and extracted with ether. The ether extract is washed with ammonium chloride, dried over magnesium sulfate and concentrated. The concentrate is distilled with the b.p. 140°/0.05 mm fraction isolated which fraction is heated at reflux with 5 ml 6 N HCl for 24 hours then evaporated to dryness. The residue is dissolved in a minimum of ethanol to which is added 150 mg of aniline, and the mixture is maintained at 0° C. for 16 hours. The resulting precipitate is filtered to give 2-acetylene-3,4-dehydroglutamic acid.

EXAMPLE 3

7-[[2-Acetylene-2-amino-4-carboxy-3,4-dehydrobutyryl]amino]-3-acetyloxymethyl-8-oxo-5-thia-1-azabicyclo[4.2.0]oct-2-ene-2-carboxylic acid A mixture of 1 gram of 3-acetyloxy-7-amino-8-oxo-5-thia-1-azabicyclo[4.2.0]oct-2-ene-2-carboxylic acid and 1 g of 2-acetylene-2-amino-4-benzyloxycarbonylbut-3-enoic acid chloride wherein the free amino group is protected with tert-butoxycarbonyl in 50 ml of ethyl acetate is refluxed for 2 hours after which the solvent is removed leaving a residue which is treated with mild acid and chromatographed on silica gel using benzene-acetone as the eluant to give 7-[[2-acetylene-2-amino-4-carboxy-3,4-dehydrobutyryl]amino]-3-acetyloxymethyl-8-oxo-5-thia-1-azabicyclo[4.2.0)oct-2-ene-2-carboxylic acid.

The following examples are illustrative of pharmaceutical preparations of compounds of general Formula I.

An illustrative composition for hard gelatin capsules is as follows:

| | |
|---|---|
| (a) 2-acetylene-3,4-dehydroglutamic acid | 10 mg |
| (b) talc | 5 mg |
| (c) lactose | 100 mg |

The formulation is prepared by passing the dry powders of (a) and (b) through a five mesh screen and mixing them well. The powder is then filled into hard gelatin capsules at a net fill of 115 mg per capsule.

EXAMPLE 5

An illustrative composition for tablet is as follows:

| | |
|---|---|
| (a) 2-acetylene-3,4-dehydroglutamic acid | 5 mg |
| (b) starch | 43 mg |
| (c) lactose | 60 mg |
| (d) magnesium stearate | 2 mg |

The granulation obtained upon mixing the lactose with the compound (a) and part of the starch and granulated with starch paste is dried, screened, and mixed with the magnesium stearate. The mixture is compressed into tablets weighing 110 mg each.

EXAMPLE 6

An illustrative composition for an injectable suspension is the following 1 ml ampul for an intramuscular injection.

| | Weight percent |
|---|---|
| (a) dimethyl 2-acetylene-3,4-dehydroglutamate | 1.0 |
| (b) polyvinylpyrrolidone | 0.5 |
| (c) lecithin | 0.25 |
| (d) water for injection to make | 100.0 |

The materials (a)–(d) are mixed, homogenized, and filled into 1 ml ampuls which are sealed and autoclaved 20 minutes at 121° C. Each ampul contains 10 mg per ml of novel compound (a).

EXAMPLE 7

Dimethyl-2-acetyleneglutamate

2-Acetylene-3,4-dehydroglutamic acid (493 mg, 2.9 mM) is added to methanol (40 ml) which is saturated with dry hydrogen chloride. The solution is heated at reflux for 12 hours, then the solvent evaporated to afford dimethyl-2-acetylene-3,4-dehydroglutamate.

EXAMPLE 8

N-Acetyl-2-acetylene-3,4-dehydroglutamic acid

To a solution of 2-acetylene-3,4-dehydroglutamic acid (340 mg, 2 mM) in 5 ml of 1 N sodium hydroxide at 0° C. are added simultaneously from 2 syringes acetyl chloride (160 mg) diluted in dioxane (1 ml) and 2 ml of 1 N sodium hydroxide. After 30 minutes at 0° C. the solution is acidified by the addition of 6 N hydrochloric acid, then extracted well with dichloromethane. The organic phase is dried and concentrated to afford N-acetyl-2-acetylene-3,4-dehydroglutamic acid.

In a similar manner, but with acetyl chloride replaced by ethyl chloroformate (220 mg), N-ethoxycarbonyl-2-acetylene-3,4-dehydroglutamic acid is obtained.

EXAMPLE 9

N,N'-Dipropyl-2-acetylene-3,4-dehydroglutamic acid biscarboxamide HBr

To a solution of 2-acetylene-3,4-dehydroglutamic acid (340 mg, 2 mM) in 5 ml of 1 N sodium hydroxide at 0° C. are added simultaneously from two syringes benzyl chloroformate (340 mg, 2 mM) in dioxane (1 ml) and 2 ml of 1 N sodium hydroxide. After 30 minutes at 0° C. the solution is acidified by the addition of 6 N hydrochloric acid, then extracted well with dichloromethane. The organic phase is dried and concentrated to afford N-(benzyloxycarbonyl)-2-ethynyl-3,4-dehydroglutamic acid. This was dissolved in dichloromethane (15 ml) and treated with thionyl chloride (238 mg) at 25° C. for one hour. Propylamine (500 mg) is then added and the solution stirred at 25° C. for one hour, then washed with water, dried and concentrated. The residue is treated with 6 ml of a solution of dioxane containing hydrogen bromide (40% w/w) and allowed to stand for 30 minutes at 25° C. Ether (50 ml) is then added and the resulting precipitate collected to afford N,N'-dipropyl-2-acetylene-3,4-dehydroglutamic acid bis-carboxamide HBr.

EXAMPLE 10

2-Acetylene-N-(2-amino-1-oxopropyl)-3,4-dehydroglutamic acid

Dimethyl-2-acetylene-3,4-dehydroglutamate (198 mg, 1 mM) in methylene chloride (4 ml) is treated with N-carbobenzoxy alanine (200 mg, 1 mM) and N,N'- dicyclohexylcarbodiimide (206 mg, 1 mM) overnight at 25° C. The mixture is then cooled to 0° C. and the precipitated dicyclohexyl urea filtered off. The filtrate is diluted with methylene chloride, washed with water, bicarbonate, dilute hydrochloric acid, then dried and concentrated. The residue is treated with ethanol (5 ml) and 5 ml of a 40% (w/w) solution of hydrogen bromide in dioxane for 30 minutes at 25° C. Ether (50 ml) is then added and the resulting precipitate collected which is treated with 1 N sodium hydroxide (15 ml) overnight at 25° C. The pH of the solution is adjusted to neutral and the product isolated from an Amberlite 120 H+ resin by elution with 2 M ammonium hydroxide affording 2-acetylene-N-(2-amino-1-oxopropyl)-3,4-dehydroglutamic acid.

We claim:

1. A compound of the formula

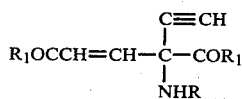

wherein each $R_1$ is the same and is hydroxy, a straight or branched alkoxy group of from 1 to 8 carbon atoms, $-NR_3R_4$ wherein each $R_3$ and $R_4$ is hydrogen or a lower alkyl group of from 1 to 4 carbon atoms and can be the same or different, or

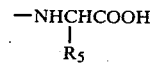

wherein $R_5$ is hydrogen, a straight or branched lower alkyl group of from 1 to 4 carbon atoms, benzyl or p-hydroxybenzyl; and R is hydrogen, alkylcarbonyl wherein the alkyl moiety has from 1 to 4 carbon atoms and is straight or branched, alkoxycarbonyl wherein the alkoxy moiety has from 1 to 4 carbon atoms and is straight or branched or

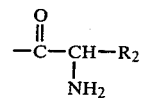

wherein $R_2$ is hydrogen, a straight or branched lower alkyl group of from 1 to 4 carbon atoms, benzyl or p-hydroxybenzyl; and pharmaceutically acceptable salts and individual optical isomers thereof.

2. A compound of claim 1 wherein each $R_1$ is hydroxy or a straight or branched alkoxy group of from 1 to 8 carbon atoms.

3. A compound of claim 1 wherein R is hydrogen or alkylcarbonyl wherein the alkyl moiety has from 1 to 4 carbon atoms and is straight or branched.

4. A compound of claim 1 wherein $R_1$ is hydroxy.

5. A compound of claim 1 wherein R is hydrogen.

6. A compound of claim 1 which is 2-acetylene-3,4-dehydroglutamic acid or a pharmaceutically acceptable salt thereof.

* * * * *